(12) United States Patent
Wang et al.

(10) Patent No.: US 8,912,247 B2
(45) Date of Patent: Dec. 16, 2014

(54) HYDROPHILIC/HYDROPHOBIC POLYMER NETWORKS BASED ON POLY(CAPROLACTONE FUMARATE), POLY(ETHYLENE GLYCOL FUMARATE), AND COPOLYMERS THEREOF

(75) Inventors: Shanfeng Wang, Knoxville, TN (US); Lichun Lu, Rochester, MN (US); Michael J. Yaszemski, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 1538 days.

(21) Appl. No.: 11/912,188

(22) PCT Filed: Apr. 28, 2006

(86) PCT No.: PCT/US2006/016156
§ 371 (c)(1),
(2), (4) Date: Jun. 20, 2008

(87) PCT Pub. No.: WO2006/118987
PCT Pub. Date: Nov. 9, 2006

(65) Prior Publication Data
US 2008/0262102 A1      Oct. 23, 2008

Related U.S. Application Data

(60) Provisional application No. 60/676,158, filed on Apr. 29, 2005.

(51) Int. Cl.
*A61L 24/04* (2006.01)
*C08G 63/60* (2006.01)
*C08G 63/83* (2006.01)
*C08G 63/676* (2006.01)
*A61L 27/18* (2006.01)

(52) U.S. Cl.
CPC ............ *C08G 63/676* (2013.01); *A61L 24/046* (2013.01); *C08G 63/60* (2013.01); *C08G 63/83* (2013.01); *A61L 27/18* (2013.01)
USPC ........... 522/179; 522/168; 522/150; 522/153; 522/154; 522/178; 522/182; 522/183; 523/105; 523/108; 523/111; 523/112; 523/113; 523/115; 514/772.3; 514/772.4; 514/772.5; 514/772.6; 623/11.11; 623/16.11; 623/23.58; 623/23.61; 623/23.75

(58) Field of Classification Search
USPC ................. 528/310; 514/772.5, 772.4, 772.6, 514/772.3; 522/168, 150, 153, 154, 178, 522/179, 182, 183; 523/105, 108, 111, 112, 523/113, 115; 623/11.11, 16.11, 23.58, 623/23.61, 23.75
See application file for complete search history.

(56) References Cited

U.S. PATENT DOCUMENTS

| | | | |
|---|---|---|---|
| 4,082,816 A | 4/1978 | Fisk et al. | |
| 4,668,295 A | 5/1987 | Bajpai | |
| 4,722,948 A | 2/1988 | Sanderson | |
| 5,085,861 A | 2/1992 | Gerhart et al. | |
| 5,490,962 A | 2/1996 | Cima et al. | |
| 5,514,378 A | 5/1996 | Mikos | |
| 5,518,680 A | 5/1996 | Cima | |
| 5,527,864 A | 6/1996 | Suggs et al. | |
| 5,644,005 A | 7/1997 | Suggs et al. | |
| 5,733,951 A | 3/1998 | Yaszemski et al. | |
| 5,747,605 A | 5/1998 | Breant et al. | |
| 5,780,426 A | 7/1998 | Palladino | |
| 5,786,217 A | 7/1998 | Tubo et al. | |
| 5,869,170 A | 2/1999 | Cima et al. | |
| 5,908,782 A | 6/1999 | Marshak et al. | |
| 6,124,373 A | 9/2000 | Peter et al. | |
| 6,153,664 A | 11/2000 | Wise et al. | |
| 6,271,278 B1 | 8/2001 | Park et al. | |
| 6,281,256 B1 | 8/2001 | Harris et al. | |
| 6,306,821 B1 | 10/2001 | Mikos | |
| 6,355,755 B1 | 3/2002 | Peter et al. | |
| 6,379,962 B1 | 4/2002 | Holy et al. | |
| 6,384,105 B1 * | 5/2002 | He et al. | 523/113 |
| 6,395,300 B1 | 5/2002 | Straub et al. | |
| 6,423,790 B1 | 7/2002 | He et al. | |
| 6,436,426 B1 | 8/2002 | Liao et al. | |

(Continued)

FOREIGN PATENT DOCUMENTS

| | | |
|---|---|---|
| CA | 1136317 | 11/1982 |
| EP | 0000507 | 2/1979 |

(Continued)

OTHER PUBLICATIONS

Temenoff et al. Effect of poly(ethylene glycol) molecular weight on tensile and swelling properties of oligo(poly(ethylene glycol) fumarate) hydrogels for cartilage tissue engineering. J. Biomedical Material Research, 2002, 59(3), 429-437.*

Payne et al. Development of an injectalbe, In Situ Crosslinkable, Degradable Polymeric Carrier for Osteogenic Cell Populations. Biomaterials, 23 pp. 4359-4371, 2002.*

Fisher et al. Photoinitiated Cross-Linking of the Biodegradable Polyester Poly (propylene fumarate). Part 1. Determination of Network Structure. Biomacromolecules (2003), 4, 1327-1334.*

(Continued)

*Primary Examiner* — Sanza McClendon
(74) *Attorney, Agent, or Firm* — Fish & Richardson P.C.

(57) ABSTRACT

Improved methods for preparing polyethylene glycol fumarate) are disclosed. Methods for chemically crosslinking or photocross-linking hydrophilic polyethylene glycol fumarate) with hydrophobic polymers such as poly(propylene fumarate) (PPF) and poly(caprolactone fumarate) (PCLF) to form various hydrogels (FIG. 1) with controllable hydrophilicity are also disclosed. The hydrogels are useful in the fabrication of injectable and in-situ hardening scaffolds for application in skeletal reconstruction. An injectable material including the hydrogels may be useful in controlled drug release.

8 Claims, 8 Drawing Sheets

(56) References Cited

U.S. PATENT DOCUMENTS

| | | | |
|---|---|---|---|
| 6,454,811 | B1 | 9/2002 | Sherwood et al. |
| 6,530,958 | B1 | 3/2003 | Cima |
| 6,562,374 | B1 | 5/2003 | Han et al. |
| 6,673,285 | B2 | 1/2004 | Ma |
| 6,753,358 | B2 | 6/2004 | Fisher et al. |
| 6,759,485 | B2 | 7/2004 | He et al. |
| 6,884,432 | B2 | 4/2005 | Yaszemski et al. |
| 6,884,778 | B2 * | 4/2005 | Jo et al. .................. 424/486 |
| 7,189,413 | B2 | 3/2007 | Calias |
| 7,309,232 | B2 | 12/2007 | Rutherford et al. |
| 7,595,043 | B2 | 9/2009 | Hedrick et al. |
| 7,629,388 | B2 * | 12/2009 | Mikos et al. ............ 514/772.3 |
| 7,642,300 | B2 | 1/2010 | Yaszemski |
| 7,816,461 | B2 * | 10/2010 | Wang et al. ............... 525/411 |
| 8,343,527 | B2 | 1/2013 | Dadsetan |
| 2001/0009662 | A1 | 7/2001 | Cohn et al. |
| 2001/0039453 | A1 | 11/2001 | Gresser et al. |
| 2001/0048945 | A1 | 12/2001 | Sankaram |
| 2002/0028189 | A1 | 3/2002 | Jo et al. |
| 2002/0177668 | A1 | 11/2002 | He et al. |
| 2003/0032733 | A1 | 2/2003 | Fisher et al. |
| 2003/0152548 | A1 | 8/2003 | Mikos et al. |
| 2004/0054410 | A1 | 3/2004 | Barrows |
| 2005/0019371 | A1 | 1/2005 | Anderson et al. |
| 2005/0058632 | A1 | 3/2005 | Hedrick et al. |
| 2005/0079470 | A1 | 4/2005 | Rutherford et al. |
| 2005/0209704 | A1 | 9/2005 | Maspero et al. |
| 2005/0251267 | A1 | 11/2005 | Winterbottom et al. |
| 2007/0043202 | A1 * | 2/2007 | Yaszemski et al. ......... 528/310 |
| 2008/0194792 | A1 | 8/2008 | Wang et al. |
| 2008/0206308 | A1 * | 8/2008 | Jabbari et al. ............. 424/426 |

FOREIGN PATENT DOCUMENTS

| | | |
|---|---|---|
| EP | 1252196 | 11/2005 |
| EP | 0877033 | 9/2007 |
| GB | 1394396 | 5/1975 |
| JP | H11-060716 | 3/1999 |
| JP | 2002-542352 | 12/2002 |
| JP | 2003-103905 | 4/2003 |
| JP | 2003-182208 | 7/2003 |
| WO | WO 95/29710 | 11/1995 |
| WO | WO 01/85180 | 11/2001 |
| WO | WO 02/062357 | 8/2002 |
| WO | WO 03/033563 | 4/2003 |
| WO | WO 2005/004811 | 1/2005 |
| WO | WO 2005/020849 | 3/2005 |
| WO | WO 2006/053031 | 5/2006 |

OTHER PUBLICATIONS

Kweon et al. A novel degradable polycarpolactone networks for tissue engineering. Biomaterials (2003) 24, pp. 801-808.*

International Search Report and Written Opinion corresponding to PCT/US2006/016156 under date of mailing of Sep. 18, 2006.

Ackery, "A global perspective on spinal cord injury epidemiology," *J. Neurotrauma*, 21(10):1355-1370, Oct. 2004.

Ahlborn et al., "One hour electrical stimulation accelerates functional recovery after femoral nerve repalr," *Exp Neurol.*, 208(1):137-144, Epub Aug. 23, 2007.

Anseth et al., "Photopolymerizable degradable polyanhydrides with osteocompatibility," *Nat Biotechnol.*, 17(2):156-159, Feb. 1999.

Arino et al., "Implantation of Schwann cells in rat tendon autografts as a model for peripheral nerve repalr: long term effects on functional recovery," *Scand J Plast Reconstr Surg Hand Surg.*, 42(6):281-285, 2008.

Ashley et al., "Therapeutic stimulation of denervated muscles: The influence of pattern," *Muscle Nerve*, 38(1):875-886, Jul. 2008.

Baltrusaitis et al., "Reactions of sulfur dioxide on calcium carbonate single crystal and particle surfaces at the adsorbed water carbonate interface," *Phys Chem Chem Phys.*, 9(23):3011-3024, Epub Feb. 28, 2007.

Behravesh and Mikos, "Three-dimensional culture of differentiating marrow stromal osteoblasts in biomimetic poly(propylene fumarate-co-ethylene glycol)-based macroporous hydrogels," *J Biomed Mater Res A*, 66(3):698-706, Sep. 1, 2003.

Chen et al., "Template synthesis of the polypyrrole tube and its bridging in vivo sciatic nerve regeneration," *J. Mat. Sci. Lett.*, 19(23):2157-2159, Nov. 2000.

Chun et al., "Controlled release of plasmid DNA from biodegradable scaffolds fabricated using a thermally-induced phase-separation method," *J. Biomater. Sci. Polymer Ed.*, 15(11):1341-1353, 2004.

Chung et al., "Syntheses and evaluation of biodegradable multifunctional polymer networks," *Eur Pol J*, 39(9):1817-1822, Sep. 2003.

Cui et al., "Advances in stem cell transplantation for spinal cord injury," *Journal of Clinical Rehabilitative Tissue Engineering Research*, 12:9335-9338, 2008.

Dadsetan et al., "Surface chemistry mediates adhesive structure, cytoskeletal organization, and fusion of macrophages," *J Biomed Mater Res A.*, 71(3):439-448, Dec. 1, 2004.

de Ruiter et al., "Methods for in vitro characterization of multichannel nerve tubes," *J Biomed Mater Res A.*, 84(3):643-651, Mar. 1, 2008.

de Ruiter et al., "Misdirection of regenerating motor axons after nerve injury and repair in the rat sciatic nerve model," *Exp Neurol.*, 211(2):339-350, Epub Jan. 8, 2008.

de Ruiter, "Accuracy of motor axon regeneration across autograft, single-lumen, and multichannel poly(lactic-co-glycolic acid) nerve tubes," *Neurosurgery*, 63(1):144-153; discussion 153-155, Jul. 2008.

Elfick, "Poly(epsilon-caprolactone) as a potential material for a temporary joint spacer," *Biomaterials*, 23(23):4463-4467, Dec. 2002.

Geremia et al., "Electrical stimulation promotes sensory neuron regeneration and growth-associated gene expression," *Exp Neurol.*, 205(2):347-359, Epub Feb. 21, 2007.

Gomez and Schmidt, "Nerve growth factor-immobilized polypyrrole: bioactive electrically conducting polymer for enhanced neurite extension," *J Biomed Mater Res A.*, 81(1):135-149, Apr. 2007.

Han et al., "Synthesis and characterization of crosslinked polymers for biomedical composites" *Journal of Macromolecular Science: Part A—Chemistry*, 25(5-7): 847-869, 1988.

Hedberg et al., "Controlled Release of an Osteogenic Peptide from Injectable Biodegradable Polymeric Composites," *J. Control. Release*, 84,137-150,2002.

Hiremath et al., "Simple setup to measure electrical properties of polymeric films," *Review of Scientific Instruments*, 77(12), 2006.

Holland et al., "In vitro release of transforming growth factor-b1 from gelatin microparticles encapsulated in biodegradable, injectable oligo(poly(ethylene glycol)fumarate) hydrogels," *J Control Release.*, 91(3):299-313, Sep. 4, 2003.

Huang et al., "Synthesis and characterization of electroactive and biodegradable ABA block copolymer of polylactide and aniline pentamer," *Biomaterials*, 28(10):1741-1751, Epub Jan. 10, 2007.

Huang et al., "Sythesis of biodegradable and electroactive multiblock polylactide and aniline pentamer copolymer for tissue engineering applications," *Biomacromolecules*, 9:850-858, 2008.

Hutmacher et al., "Scaffold-based tissue engineering: rationale for computer-aided design and solid free-form fabrication systems," *Trends in Biotech*, 22(7):354-362, Jul. 2004.

Jabbari et al., "Development of a novel self-crosslinkable poly (caprolactone fumarate) as a biodegradable and injectable scaffold for bone tissue engineering," *Proceedings of the 25th Annual International Conference of the IEEE Engineering in Medicine and Biology Society*, 2:1219-1222, 2003.

Jabbari et al., "Synthesis, material properties, and biocompatibility of a novel self-crosslinkable poly(caprolactone fumarate) as an injectable tissue engineering scaffold," *Biomacromolecules*, 6(5):2503-2511, Sep.-Oct. 2005.

Jo et al., "Modification of oligo(poly(ethylene glycol) fumarate) macromer with a GRGD peptide for the preparation of functionalized polymer networks," *Biomacromolecules*, 2(1):255-261, Spring 2001.

Jo et al., "Synthesis and Characterization of Oligo(poly(ethylene glycol) fumarate) Macromer," *Macromolecules*, 34(9): 2839-2844, 2001.

Kam et al., "Electrical stimulation of neural stem cells mediated by humanized carbon nanotube composite made with extracellular matrix protein," *Nano Lett.*, 9(1):273-278, Jan. 2009.

(56) References Cited

OTHER PUBLICATIONS

Kemp et al., "Growth factor and stem cell enhanced conduits in peripheral nerve regeneration and repair," *Neurol Res.*, 30(10):1030-1038, Dec. 2008.
Kotwal and Schmidt, "Electrical stimulation alters protein adsorption and nerve cell interactions with electrically conducting biomaterials," *Biomaterials*, 22(10):1055-1064, May 2001.
Lang et al., "Functionalized multiarm poly (-caprolactone): Synthesis, structure analysis, and network formation," *J. Applied Polymer Science*, 86(9):2296-2306, ePub Sep. 18, 2002.
Lee et al., "Carboxy-endcapped conductive polypyrrole:biomimetic conducting polymer for cell scaffolds and electrodes," *Langmuir*, 22(24):9816-9819, Nov. 21, 2006.
Lee, "Carboxylic acid-functionalized conductive polypyrrole as a bioactive platform for cell adhesion," *Biomacromolecules*, 7(6):1692-1695, Jun. 2006.
Li et al., "Direct-current electrical field guides neuronal stem/progenitor cell migration," *Stem Cells*, 26(8):2193-2200, Epub Jun. 12, 2008.
Mao et al., "New biocompatible polypyrrole-based films with good blood compatibility and high electrical conductivity," *Colloids Surf B Biointerfaces*, 67(1):41-45, Epub Aug. 3, 2008.
Moore et al., "Multiple-channel scaffolds to promote spinal cord axon regeneration," *Biomaterials*, 27(3):419-429, Epub Aug. 31, 2005.
Ng et al., "Evaluation of ultra-thin poly(epsilon-caprolactone) films for tissue-engineered skin," *Tissue Eng.*, 7(4):441-455, Aug. 2001.
Park et al., "Characterization of porous collagen/hyaluronic acid scaffold modified by 1-ethyl-3-(3-dimethylaminopropyl)carbodiimide cross-linking," *Biomaterials*, 23(4):1205-1212, Feb. 15, 2002.
Park et al., "Electrical pulsed stimulation of surfaces homogeneously coated with gold nanoparticles to induce neurite outgrowth of PC12 cells," *Langmuir*, 25(1):451-457, Jan. 6, 2009.
Peter et al., "Crosslinking characteristics of an injectable poly(propylene fumarate)/beta-tricalcium phosphate paste and mechanical properties of the crosslinked composite for use as a biodegradable bone cement" *J Biomed Mater Res.*, 44(3):314-321, Mar. 5, 1999.
Runge et al., "Fabrication of conducting composite materials of polypyrrole-polycaprolactone fumarate for nerve regeneration," *Polymer Preprints*, 50(1):313-314, 2009.
Sago et al., "In vitro differentiation of canine celiac adipose tissue-derived stromal cells into neuronal cells,"*J Vet Med Sci.*, 70(4):353-357, Apr. 2008.
Schmidt et al., "Stimulation of neurite outgrowth using an electrically conducting polymer," *Proc Natl Acad Sci U S A.*, 94(17):8948-8953, Aug. 19, 1997.
Shi et al., "A novel electrically conductive and biodegradable composite made of polypyrrole nanoparticles and polylactide," *Biomaterials*, 25(13):2477-2488, Jun. 2004.
Shi et al., "Electrical stimulation enhances viability of human cutaneous fibroblasts on conductive biodegradable substrates," *J Biomed Mater Res A.*, 84(4):1026-1037, Mar. 15, 2008.
Shi et al., "The regulation of cell functions electrically using biodegradable polypyrrole-polylactide conductors," *Biomaterials*, 29(28):3792-3798, Epub Jul. 7, 2008.
Shin et al., "In vivo bone and soft tissue response to injectable, biodegradable oligo(poly(ethylene glycol) fumarate) hydrogels," *Biomaterials.*, 24(19):3201-3211, Aug. 2003.
Shin et al., "Modulation of marrow stromal osteoblast adhesion on biomimetic oligo[poly(ethylene glycol) fumarate] hydrogels modified with Arg-Gly-Asp peptides and a poly(ethyleneglycol) spacer,"*J Biomed Mater Res.*, 61(2):169-179, Aug. 2002.
Shustak et al., "A novel electrochemically synthesized biodegradable thin film of polypyrrole-polyethyleneglycol-polylactic acid nanoparticles," *New J. Chem.*, 31(1):163-168, 2007.
Song et al., "Peripheral Nerve: What's New in Basic Science Laboratories," *Neurosurg Clin N Am.*, 20(1):121-131, Jan. 2009.

Storey et al., "Synthesis and free radical curing of poly(epsilon-caprolactone-co-D,L-lactide) fumarate" *Polymer Preprints*, Division of Polymer Chemistry, Inc, American Chemical Society, 32(1):629-630, 1991.
Storey et al., "Bioabsorbable composites. I: Fundamental design considerations using free radically crosslinkable matrices," *Polymer Composites*, 14(1):7-16, Feb. 1993.
Tabesh, "The role of biodegradable engineered scaffolds seeded with Schwann cells for spinal cord regeneration," *Neurochem Int.*, 54(2):73-83, Epub Nov. 25, 2008.
Taylor et al., "The incidence of peripheral nerve injury in extremity trauma," *Am J Phys Med Rehabil.*, 87(5):381-385, May 2008.
Temenoff et al., "Thermally cross-linked oligo(poly(ethylene glycol) fumarate) hydrogels support osteogenic differentiation of encapsulated marrow stromal cells in vitro," *Biomacromolecules*, 5(1):5-10, published online on Nov. 26, 2003.
Vivó et al., "Immediate electrical stimulation enhances regeneration and reinnervation and modulates spinal plastic changes after sciatic nerve injury and repair," *Exp Neurol.*, 211(1):180-193, Epub Feb. 13, 2008.
Wang et al., "Evaluation of biocompatibility of polypyrrole in vitro and in vivo," *J Biomed Mater Res A.*, 68(3):411-422, Mar. 1, 2004.
Wang et al., "In vivo evaluation of a novel electrically conductive polypyrrole/poly(D,L-lactide) composite and polypyrrole-coated poly(D,L-lactide-co-glycolide) membranes," *J Biomed Mater Res A.*, 70(1):28-38, Jul. 1, 2004.
Wang et al., "Photo-crosslinked poly(epsilon-caprolactone fumarate) networks for guided peripheral nerve regeneration: material properties and preliminary biological evaluations," *Acta Biomater.*, 5(5):1531-1542, Epub Jan. 7, 2009.
Wang, "Synthesis and characterizations of biodegradable and crosslinkable poly(e-caprolactone fumarate), poly(ethylene glycol fumarate), and their amphiphilic copolymer," *Biomaterials*, 27(6):832-841, Epub Aug. 15, 2005.
Wiggins "Design of bioabsorbable, amorphous polymer networks and composites," PhD Thesis Abstract, University of Southern Mississippi, Hattiesburg, MS, 1992 [retrieved on Mar. 12, 2014]. Retrieved from the Internet <URL: http://www.osti.gov/scitech/biblio/7153129>, 2 pages.
Xie et al., "Experimental investigation on the reliability of routine SEC-MALLS for the determination of absolute molecular weights in the oligomeric range," *Polymer*, 43(14):3973-3977, Jun. 2002.
Xie, De-Liang, et al., "Synthesis and characterization of novel carboxyl telechelic microspheres" *J. Applied Polymer Science*,68(2): 205-216, Apr. 11, 1998.
Yang et al. "The design of scaffolds for use in tissue engineering. Part I. Traditional factors," *Tissue Eng.*, 7(6):679-689, Dec. 2001.
Yao et al., "Small applied electric fields guide migration of hippocampal neurons," *J Cell Physiol.*, 216(2):527-535, Aug. 2008.
Yaszemski et al., "Clinical needs for bone tissue engineering technology," Ed. Davis, *Bone Engineering*, 541-547, 2000.
Zhang et al., "Electrically conductive biodegradable polymer composite for nerve regeneration: electricity-stimulated neurite outgrowth and axon regeneration," *Artif Organs.*, 31(1):13-22, Jan. 2007.
European Search Report and Written Opinion for EP App. No. 05851461.3, completed Oct. 5, 2010, 5 pages.
European Search Report and Written Opinion for EP App. No. 05851973, completed Jun. 9, 2010, 4 pages.
European Search Report and Written Opinion for EP App. No. 06748605, completed Jun. 8, 2010, 5 pages.
European Search Report and Written Opinion for EP App. No. 06751721, completed Apr. 14, 2009, 3 pages.
European Search Report for EP 1 664 168, Application No. EP 04 78 2412, dated Aug. 9, 2006, 2 pages.
European Search Report for EP App. No. 04777316, completed Mar. 3, 2008, 3 pages.
European Search Report for EP App. No. 04782412, completed Aug. 9, 2006, 2 pages.
International Preliminary Report on Patentability for PCT/US2004/021040, issued Jan. 3, 2006, 5 pages.

(56) References Cited

OTHER PUBLICATIONS

International Preliminary Report on Patentability for PCT/US2004/027926, issued Feb. 28, 2006, 4 pages.
International Preliminary Report on Patentability for PCT/US2005/040571, issued May 15, 2007, 5 pages.
International Preliminary Report on Patentability for PCT/US2005/042240, issued May 22, 2007, 5 pages.
International Preliminary Report on Patentability for PCT/US2006/010629, issued Sep. 25, 2007, 4 pages.
International Preliminary Report on Patentability for PCT/US2006/016156, issued Oct. 30, 2007, 8 pages.
International Search Report and Written Opinion for PCT/US2004/021040, mailed Dec. 15, 2005, 5 pages.
International Search Report and Written Opinion for PCT/US2004/027926, mailed May 10, 2005, 4 pages.
International Search Report and Written Opinion for PCT/US2004/020842, mailed Dec. 16, 2004, 5 pages.
International Search Report and Written Opinion for PCT/US2005/042240, mailed Jun. 21, 2006, 7 pages.
International Search Report and Written Opinion for PCT/US2005/40571, mailed Jul. 13, 2006, 7 pages.
International Search Report and Written Opinion for PCT/US2006/010629, mailed Aug. 24, 2006, 4 pages.

* cited by examiner

Figure 2. Schematic crosslinking and swelling process of PEGF and PCLF.

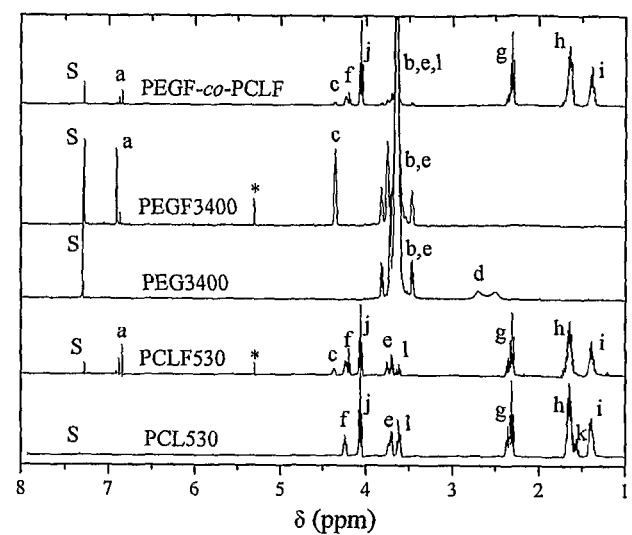
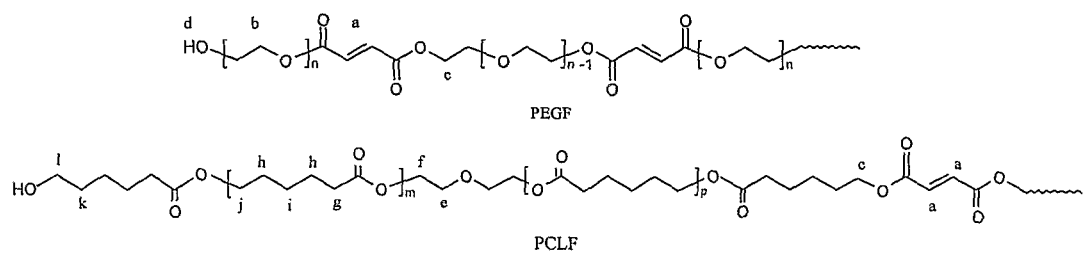
FIGURE 4

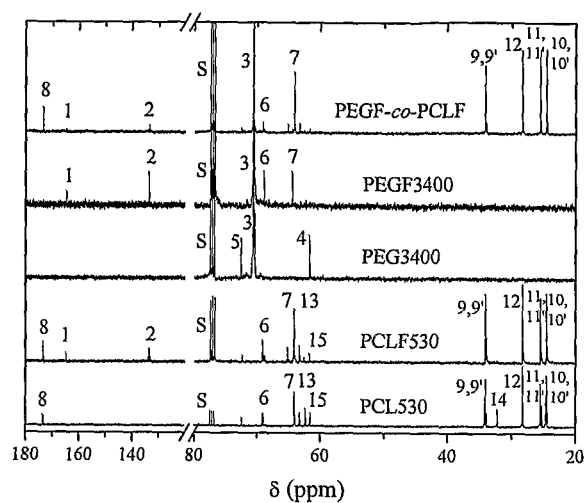
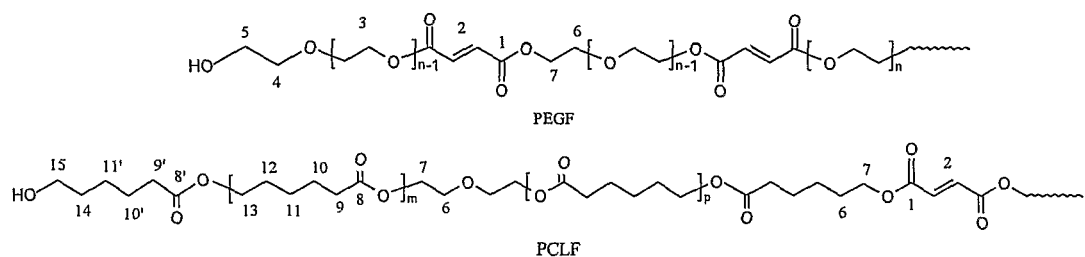
FIGURE 5

HYDROPHILIC/HYDROPHOBIC POLYMER NETWORKS BASED ON POLY(CAPROLACTONE FUMARATE), POLY(ETHYLENE GLYCOL FUMARATE), AND COPOLYMERS THEREOF

CROSS-REFERENCES TO RELATED APPLICATIONS

This application claims priority from U.S. Provisional Patent Application No. 60/676,158 filed Apr. 29, 2006.

This invention was made with government support under grant numbers AR045871 and EB003060 awarded by the National Institutes of Health. The government has certain rights in the invention.

BACKGROUND OF THE INVENTION

1. Field of the Invention

This invention relates to improved methods for preparing poly(ethylene glycol fumarate) and to methods for chemically crosslinking or photocrosslinking poly(ethylene glycol fumarate) with hydrophobic polymers such as poly(propylene fumarate) and poly(caprolactone fumarate) to form various hydrogels with controllable hydrophilicity. The hydrogels are useful as a biocompatible, bioresorbable, injectable, and in-situ hardening scaffold for tissue engineering applications and for controlled drug release applications.

2. Description of the Related Art

The clinical needs for bone regeneration are diverse, and there are roughly 1,000,000 patients who have skeletal defects each year in the United States that require bone graft procedures to achieve union. These include applications arising from resection of primary and metastatic tumors, bone loss after skeletal trauma, primary and revision total joint arthroplasty with bone deficiency, spinal arthrodesis, and trabecular voids following osteoporotic insufficiency fractures.

Current clinical methods of treating skeletal defects involve bone transplantation or the use of other materials to restore continuity. Autologous bone graft has been the gold standard of bone replacement because it provides such essential elements as osteogenic cells, osteoinductive factors, and an osteoconductive matrix for healing. However, the limited supply of autograft bone, and donor site morbidity both restrict the spectrum of cases in which it can be used alone. Allograft bone, although available in abundant supply, has drawbacks that include reduced rates of graft incorporation compared to autograft bone, and the possibility of pathogen transfer from donor to host.

Metals provide immediate mechanical support at the defect site but exhibit less than ideal overall integration with host tissue and can eventually fail due to fatigue loading if the bone does not heal prior to fatigue failure of the metal. Ceramics, such as β-tricalcium phosphate (β-TCP) and hydroxyapatite are both osteoconductive, and have found clinical use as surface coatings on metal prostheses to enhance bonding of those prostheses to bone. In particulate form, they offer increased mechanical strength to polymeric composite materials primarily in compression, but are less effective in enhancing resistance to torsional and bending forces. Poly(methyl methacrylate) bone cement can be injected or molded and is sometimes used to fill both cavitary and segmental defects, such as those that result from the curettage of a giant cell tumor or from the resection of a vertebral body in metastatic disease to the spine, respectively. However, the temperature can rise up to 100° C. during the exothermic polymerization reaction, and the heat released risks local tissue injury. Additionally, poly(methyl methacrylate) is non-biodegradable and can thus accumulate fatigue damage with time and eventually undergo mechanical failure.

Synthetic biodegradable polymers may provide treatment options not currently available. These materials can be manufactured in virtually unlimited supply and the flexibility in their design allows the synthesis of a wide range of polymers with varying mechanical, biologic, degradation, and rheologic properties. For instance, their mechanical and degradation properties can be manipulated by changing the polymer molecular weight during synthesis, and can thus be tailored to fit a particular application. The injectable nature of the skeletal regeneration biomaterial would be ideal to fill defects with limited accessibility or irregular shape. For example, minimally invasive endoscopic techniques now in clinical use would allow the injectable form of the biomaterial to be inserted for posterolateral intertransverse process spinal fusion. This would decrease the surgical trauma from the extensive exposure and muscle stripping that must now be done to put the graft material into position. The injectable material could be placed into cancellous voids from periarticular fractures, osteoporotic spinal fractures, or bone cysts without creating a large access hole in the surrounding cortical bone. These clinical situations represent the motivation for the development of injectable biodegradable polymeric materials for bone tissue engineering.

Controlled release of bioactive molecules such as drugs and growth factors has also become an important aspect of tissue engineering because it allows modulation of cellular function and tissue formation at the afflicted site. The encapsulation of drugs, proteins and other bioactive agents within biodegradable materials is an effective way to control the release profile of the contained substance.

Recently developed injectable materials and hydrogels have fulfilled many design criteria for these diverse medical applications. A polyethylene glycol (PEG) derivative, poly(ethylene glycol fumarate) (PEGF), has been developed as an injectable in-situ crosslinkable and biodegradable hydrogel (see Jo, *Macromolecules* 2001, 34, 2839; U.S. Pat. No. 6,884, 778; and U.S. Patent Application Publication No. 2002/0028189). PEGF is a hydrophilic oligomer of PEG with fumarate moieties synthesized by condensation polymerization of polyethylene glycol with fumaryl chloride. The fumarate groups in this macromer allow for crosslinking in-situ as well as degradation via hydrolysis. A chemical initiation system consisting of ammonium persulfate and ascorbic acid is used to form hydrogels without the need for ultraviolet light (see Temenoff, *J. Biomed. Mater. Res.* 2001, 59, 429). The attachment of marrow stromal cells (MSCs) on PEGF hydrogel has been investigated with a model cell adhesion specific peptide (see Shin, *J. Biomed. Mater. Res.* 2002, 61, 169). The model RGD peptide was incorporated into PEGF hydrogel after being coupled to acrylated PEG of molecular weight 3400 g·mol$^{-1}$ (see Jo et al., "Modification of Oligo(poly(ethylene glycol) fumarate) Macromer with a GRGD Peptide for the Preparation of Functionalized Polymer Networks", *Biomacromolecules* 2001, 2, 255).

By altering the PEG chain length of PEGF, the crosslink density, or the initial peptide concentration, hydrogels with a wide variety of physical properties can be synthesized. As the peptide concentration is increased the attachment of MSCs to PEGF hydrogels with PEG molecular weights of 930 and 2860 g mol$^{-1}$ increased. However, the number of attached MSCs to a PEGF hydrogel of PEG molecular weight of 6090 g mol$^{-1}$ remained constant regardless of the peptide density. The length of PEG chain in PEGF also influenced the degree of cell attachment. For example, when 1 mmol peptide/g of PEGF hydrogel was incorporated into the PEGF, the degree of cell attachment relative to initial seeding density was 93.9±5.9%, 64.7±8.2%, and 9.3±6.6% for PEGF with PEG molecular weights of 930, 2860, and 6090 g mol$^{-1}$, respectively. On the other hand, the crosslinking density of the PEGF hydrogel did not significantly affect cell attachment. The interaction was sequence specific because MSC attachment to a RGD modified hydrogel was competitively inhibited when cells were incubated in the presence of soluble RGD prior to cell seeding. These results indicate that altering the peptide concentration can modulate cell attachment to a PEGF hydrogel. PEGF macromer has also been crosslinked with N,N'-methylene bisacrylamide (MBA) to fabricate injectable scaffolds which crosslink in-situ as a cell carrier for mesenchymal stem cells (see Jabbari, 14*th Int Symp. Microencap. Proceed.* 2000, 54). This system is potentially useful for treatment of osteochondoral defects. A novel combination of redox initiators consisting of ammonium persulfate and N,N,N',N'-tetramethylethylenediamine (TMED) was used in this system to obtain a neutral pH. Mesenchymal stem cells (MSCs) were successfully seeded in this injectable system. The encapsulated MSCs cultured in complete osteogenic media showed alkaline phosphatase activity and increase in mineralized matrix for up to 21 days.

Poly(propylene fumarate) (PPF) is an unsaturated linear polyester that can be modified or crosslinked through its fumarate double bonds. See, for example, U.S. Pat. No. 5,733,951. Poly(ε-caprolactone) (PCL) is a well-known biodegradable polymer and FDA-approved for use as resorbable sutures. It has excellent biocompatibility and flexibility. PCL was recently studied as a potential material for a temporary joint spacer (see Elfick, *Biomaterials*, 2002, 23, 4463-7) and tissue engineered skin (see Ng, *Tissue Engineering*, 2001, 7, 441-55). There has been developed a copolymer based on PCL and fumarate segments, poly(caprolactone fumarate) (PCLF). Due to the presence of PCL unit, the PCLF chain is much more flexible than the PPF chain. This renders PCLF self-crosslinkable without the use of any crosslinkers. See PCT International Publication No. WO 2005/004811.

Photocrosslinking is the formation of a covalent linkage between two macromolecules or between two different parts of one macromolecule. Photocrosslinking allows in vivo curing, which provides great flexibility for the placement and handling of implantable polymers for surgeons. The main advantages of photocrosslinking over other crosslinking techniques are spatial and temporal control of the polymerization, fast curing rates at room temperature, and ease of fashioning and flexibility during implantation (see Anseth, *Nature Biotechnology*, 1999, 17, 156-9).

The major shortcomings of previous poly(ethylene glycol fumarate) (PEGF) synthesis methods are the dark color of the PEGF product and the relatively low efficiency of reaction due to the proton scavenger triethylamine in the polycondensation.

Accordingly, there is a need for improved methods for preparing poly(ethylene glycol fumarate). Also, there is a need for methods for chemically crosslinking or photo-crosslinking poly(ethylene glycol fumarate) with hydrophobic polymers such as poly(propylene fumarate) (PPF) and poly(caprolactone fumarate) (PCLF) to form various hydrogels with controllable hydrophilicity as well as controlled swelling and mechanical properties.

SUMMARY OF THE INVENTION

In this invention, poly(ethylene glycol fumarate) is prepared using a metal salt proton scavenger, preferably, an alkali metal carbonate proton scavenger, and most preferably potassium carbonate. The invention has modified PEGF synthesis processes to make the time consumption much shorter and the molecular weights of the final products higher. For example, the method can prepare poly(ethylene glycol fumarate) having a weight average molecular weight greater than 5000 g mol$^{-1}$.

The newly synthesized PEGF can be chemically crosslinked or photocrosslinked with itself or unsaturated, hydrophobic polymers such as poly(propylene fumarate) (PPF) and poly(caprolactone fumarate) (PCLF) to form various hydrogels with controllable hydrophilicity as well as swelling and mechanical properties. The hydrogels may be useful in the fabrication of injectable and in-situ hardening scaffolds for application in skeletal reconstruction.

In addition, the invention provides a process for preparing a copolymer (PEGF-co-PCLF) including caprolactone fumarate units and ethylene glycol fumarate units.

An injectable material including the hydrogels may also be useful in various research and clinical aspects, particularly, controlled drug release. For example, one or more bioactive agents can be added to the hydrogels or entrapped in the hydrogel particles. The bioactive agent or bioactive agents are selected depending on the physiological effect desired.

These and other features, aspects, and advantages of the present invention will become better understood upon consideration of the following detailed description, drawings, and appended claims.

BRIEF DESCRIPTION OF THE DRAWINGS

FIG. 4 shows a $^1$H NMR (400.1 MHz, CDCl$_3$, reference TMS) spectra of PCL530, PCLF530, PEG3.4K, PEGF3.4K, and PEGF-co-PCLF where S=solvent, and asterisks indicate signals due to methylene chloride.

FIG. 5 shows a $^{13}$C NMR (100.6 MHz, CDCl$_3$, reference TMS) spectra of PCL530, PCLF530, PEG3.4K, PEGF3.4K, and PEGF-co-PCLF where S=solvent.

DETAILED DESCRIPTION OF THE INVENTION

Figure 1:
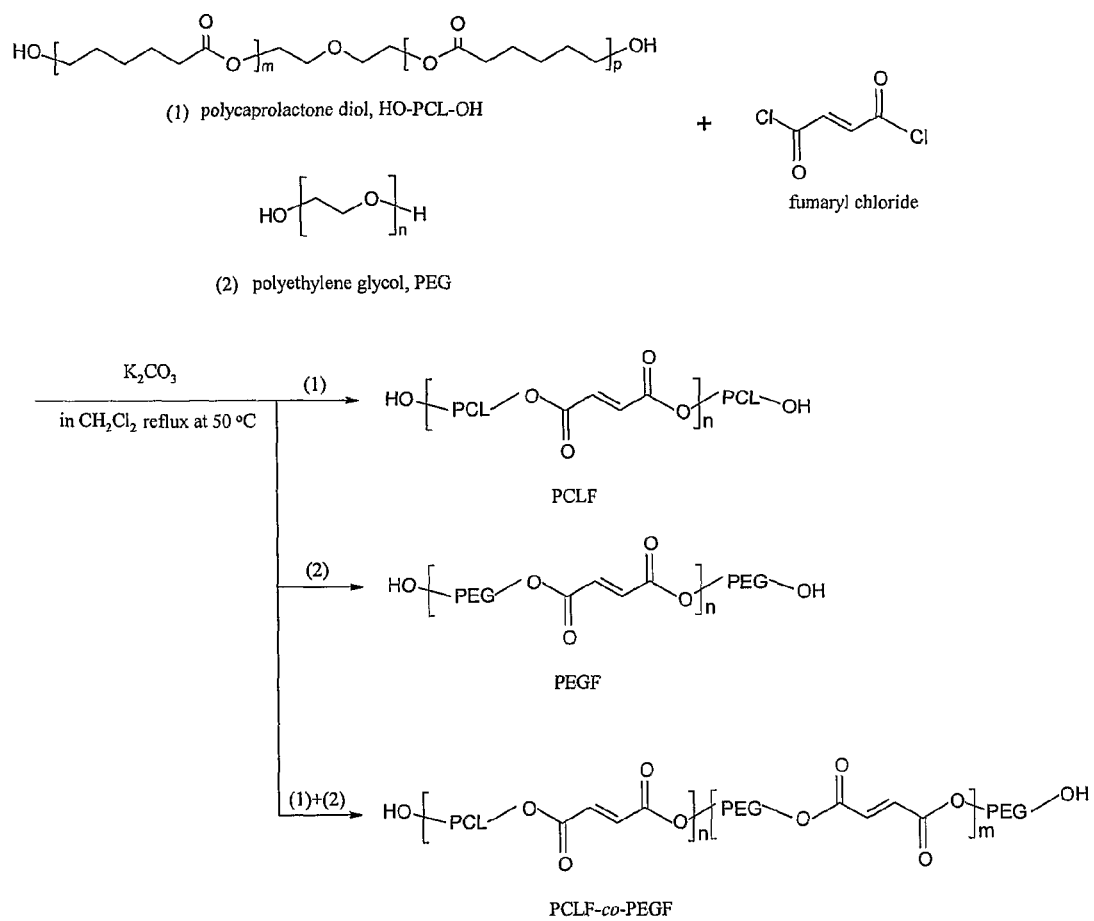
FIG. 1 shows synthesis schemes of poly(caprolactone fumarate) (PCLF), poly(ethylene glycol fumarate) (PEGF), and PEGF-co-PCLF.
Figure 2:
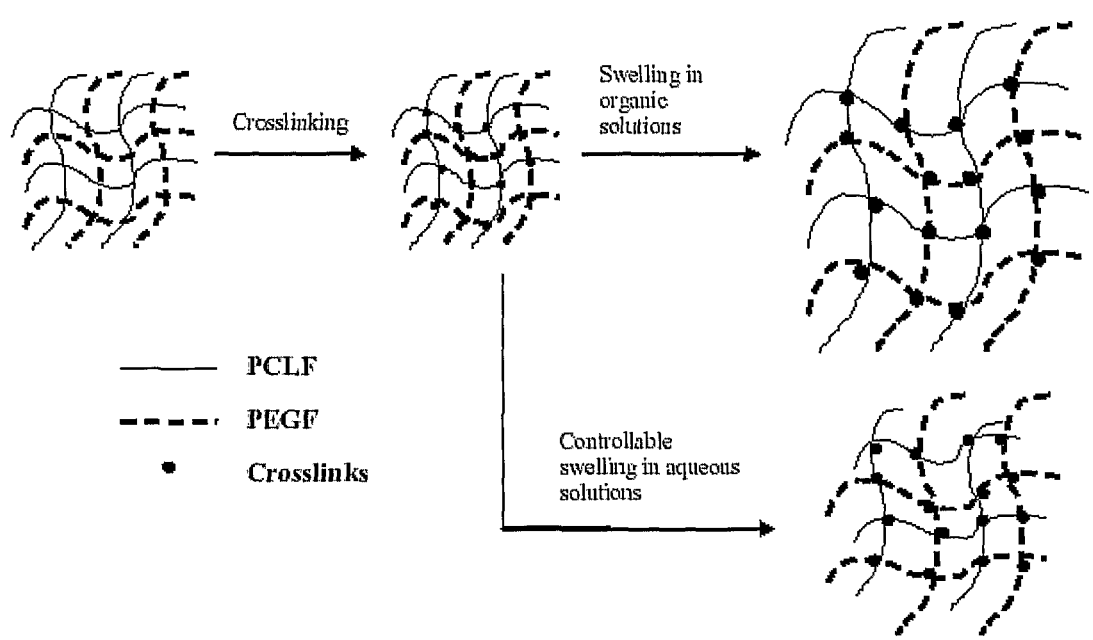
FIG. 2 shows a schematic crosslinking and swelling process of poly(ethylene glycol fumarate) (PEGF) and poly(caprolactone fumarate) (PCLF).
Figure 3:
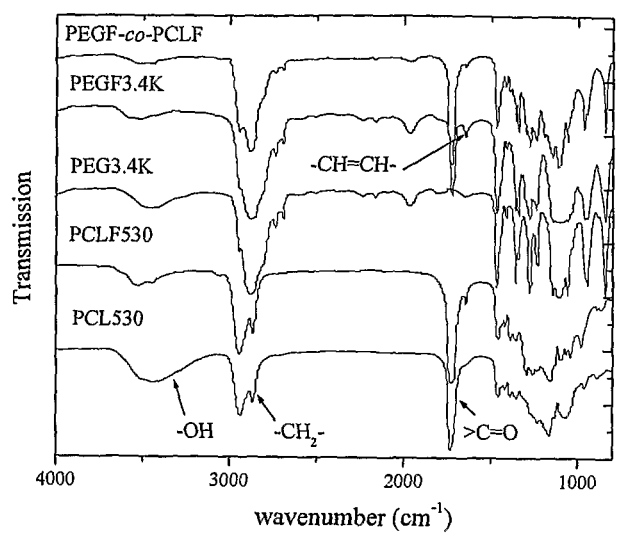
FIG. 3 shows Fourier Transform Infrared Spectroscopy (FTIR) spectra of PCL530, PCLF530, PEG3.4K, PEGF3.4K, and PEGF-co-PCLF.
Figure 6:
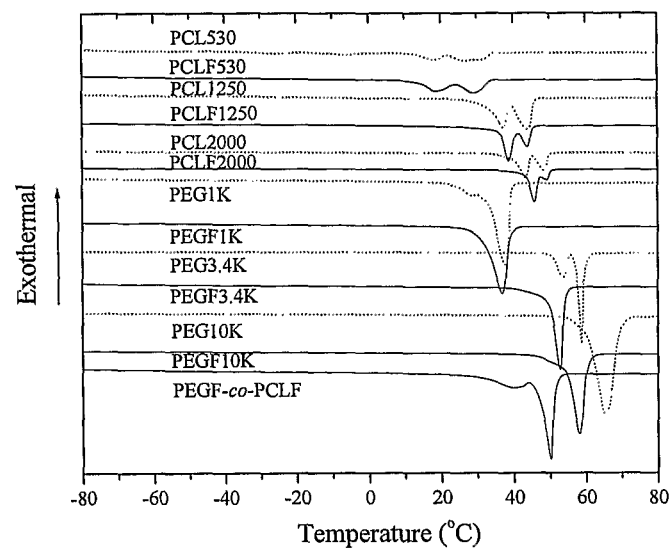
FIG. 6 shows differential scanning calorimetery (DSC) curves of example polymers described herein.
Figure 7:
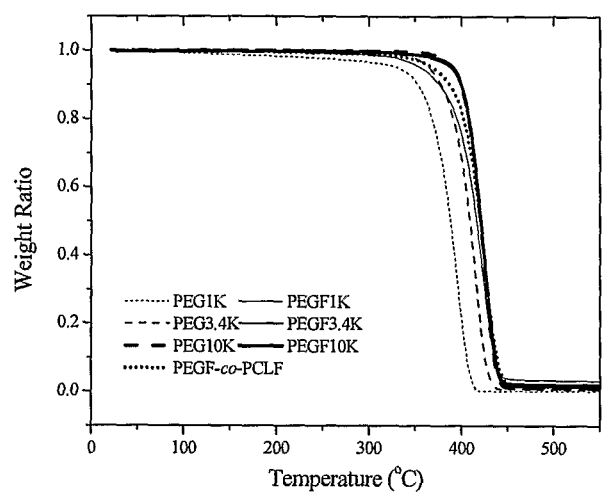
FIG. 7 shows thermogravimetric analysis (TGA) thermograms of PEGF, PEG, and PEGF-co-PCLF.

In one aspect, the invention provides a method for preparing poly(ethylene glycol fumarate). In the method, polyethylene glycol is reacted with fumaric acid or a salt thereof (e.g. fumaryl chloride) in the presence of a metal salt. The metal salt may be an alkali metal salt, preferably an alkali metal carbonate, and most preferably potassium carbonate. The method avoids the formation of a dark colored product as in prior methods. Also, the method can prepare poly(ethylene glycol fumarate) having a weight average molecular weight greater than 5000 g mol$^{-1}$.

In another aspect, the invention provides a copolymer including caprolactone fumarate units and ethylene glycol fumarate units, and a process for preparing the PEGF-co-PCLF copolymer. The ethylene glycol fumarate unit is hydrophilic and the caprolactone fumarate unit is hydrophobic rendering the PEGF-co-PCLF copolymer amphiphilic. This offers one approach to control the swelling ratio of hydrogels by modulating the compositions and block lengths of both the hydrophilic and hydrophilic components. An example copolymer has the formula:

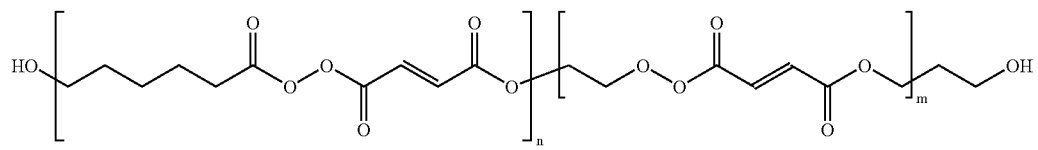

wherein n and m are integers.

The PEGF-co-PCLF may be prepared by reacting a polycaprolactone diol, polyethylene glycol, and fumaric acid or a salt thereof. The PEGF-co-PCLF may also be prepared by reacting (i) a first polymer prepared by reacting a polycaprolactone diol and fumaric acid or a salt thereof, and (ii) a second polymer prepared by reacting polyethylene glycol and fumaric acid or a salt thereof. The copolymer may be incorporated into a crosslinkable, biodegradable material useful in preparing a scaffold for tissue regeneration.

In yet another aspect, the invention provides a biodegradable material including poly(ethylene glycol fumarate) crosslinked with poly(propylene fumarate) that is useful as a scaffold for tissue regeneration. The material may be formed from a crosslinkable, biodegradable material including poly(ethylene glycol fumarate), poly(propylene fumarate), and a free radical initiator or photoinitiator. Preferably, the material is self-crosslinkable. The material may be photocrosslinkable. In one form, the material is an injectable bone substitute.

In still another aspect, the invention provides a biodegradable material including poly(ethylene glycol fumarate) crosslinked with poly(caprolactone fumarate) that is useful as a scaffold for tissue regeneration. The material may be formed from a crosslinkable, biodegradable material including poly(ethylene glycol fumarate), poly(caprolactone fumarate), and a free radical initiator or photoinitiator. Preferably, the material is self-crosslinkable. The material may be photocrosslinkable. In one form, the material is an injectable bone substitute.

Thus, the invention provides photocrosslinkable, biodegradable materials useful in preparing a scaffold for tissue regeneration. As described above, example materials according to the invention include (i) a copolymer including caprolactone fumarate units and ethylene glycol fumarate units, (ii) a poly(ethylene glycol fumarate) and poly(caprolactone fumarate) blend, or (iii) a poly(ethylene glycol fumarate) and poly(propylene fumarate) blend. The photocrosslinkable, biodegradable materials include a photoinitiator such as benzoin and benzoin ether compounds, benzil ketal compounds, acetophenone compounds, aminoalkylphenone compounds, hydroxyalkylphenone compounds, acylphosphine oxides, acylphosphine sulfides, phenylglyoxylate compounds, benzophenone compounds, thioxanthone compounds, and mixtures thereof. In one example material, the photoinitiator is bisacylphosphinoxide.

The material may be an injectable bone substitute or an injectable bone cement. The injectable nature of the material allows for the filling of defects of limited accessibility or irregular shape. For example, minimally invasive endoscopic techniques now in clinical use may allow the injectable form of the material to be inserted for posterolateral intertransverse process spinal fusion. The injectable material could be placed into cancellous voids from periarticular fractures, osteoporotic spinal fractures, or bone cysts without creating a large access hole in the surrounding cortical bone.

With respect to the injectable nature of materials according to the invention, the temperature range of injection can be broad, between the melting point of the mixture and the boiling point of the solvent used in the mixture. Normally the polymer mixture is injected at room temperature for convenience.

Because the biodegradable material according to the invention may be self-crosslinking, the material does not need to include a crosslinker. A crosslinker is typically used to help bridge the neighboring double bonds in crosslinking. Because the self-crosslinkable and/or photocrosslinkable, biodegradable material according to the invention does not need any crosslinkers, toxicity concerns in biomedical applications are minimized; however, a crosslinker can used. An example crosslinker would be an acrylate monomer.

The crosslinkable material according to the invention is suitable for forming a scaffold for tissue regeneration. In one form, the crosslinkable material includes a porogen to allow for the formation of a porous scaffold. Suitable porogens include salt crystals (e.g., sodium chloride) that may be used in a salt leaching technique that forms a porous scaffold. Examples of this type of particle leaching technique can be found in U.S. Pat. Nos. 6,436,426, 6,379,962 and 5,514,378. The porogen may also be a hydrogel porogen as described in PCT International Publication No. WO 2005/020849. The choice of porogen may be dictated by the crosslinking process. Porogens can be used in making a crosslinked film; however, it depends the physical properties and color of the porogen. Also, some porogens may block the UV light thereby make the photocrosslinking procedure inefficient. Thus, the photocrosslinkable, biodegradable material according to the invention may or may not include a porogen depending on the final product desired.

The crosslinkable material may further include particulate or fiber reinforcement materials. Hydroxyapatite is especially advantageous to serve as a reinforcement material because of its similarity in composition to bone mineral, bioactivity and promotion of cellular function, and osteoconductivity. The reinforcement materials may also comprise single-wall carbon nanotubes.

The crosslinkable material may further include one or more bioactive agents. A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, and therapeutics.

The crosslinkable biodegradable material may also include an accelerator. Non-limiting example accelerators include toluidines (such as N,N-diethyl-p-toluidine ("DET") and N,N-dimethyl-o-toluidine ("DMT")), acetyl phenylhydrazine, maleic acid, quinines (such as napthaquinone and anthraquinone), and alkyl mercaptans. Often, in a photocrosslinking process, an accelerator is not needed because the whole procedure is rather short (e.g., less than 30 minutes).

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. As used herein, a "bioresorbable" material is one that breaks down over a finite period of time due to the chemical/biological action of the body. By "injectable", we mean the copolymer may be delivered to a site by way of a medical syringe. By "self-crosslinkable", we mean the functional groups of a polymer according to the invention may crosslink with the functional groups of the same polymer or another polymer according to the invention without a crosslinking agent that forms crosslinks between the functional groups of a polymer according to the invention and the functional groups of the same or another polymer according to the invention. By "photocrosslinkable", we mean the functional groups of a copolymer according to the invention may crosslink with the functional groups of the same polymer or another copolymer according to the invention by application of photons (e.g., UV light) in the presence of a photoinitiator.

The term "molecular weight" in this specification refers to "weight average molecular weight" ($M_w = \Sigma_i N_i M_i^2 / \Sigma_i N_i M_i$). Although weight average molecular weight ($M_w$) can be determined in a variety of ways, with some differences in result depending upon the method employed, it is convenient to employ gel permeation chromatography. As used herein, the term "number average molecular weight" ($M_n$) refers to the total weight of all the molecules in a polymer sample divided by the total number of moles present ($M_n = \Sigma_i N_i M_i / \Sigma_i N_i$). Although number average molecular weight can be determined in a variety of ways, with some differences in result depending upon the method employed, it is convenient to employ gel permeation chromatography. As used herein, the term "polydispersity" refers to the ratio of a materials' "weight average molecular weight" divided by its "number average molecular weight" ($M_w / M_n$).

EXAMPLES

The following Examples have been presented in order to further illustrate the invention and are not intended to limit the invention in any way.

A. Synthesis of Poly(ethylene glycol fumarate) (PEGF) Macromers

Poly(ethylene glycol)s (PEGs, Aldrich) were dried by an azeotropic distillation in toluene and then evacuated under reduced pressure to remove residual traces of water. Fumaryl chloride, PEG, and potassium carbonate were measured out in a molar ratio of 1:1:1.5. The polymer density of PEG3.4K is 1.0926 g·cm$^{-3}$. The PEG was dissolved in methylene chloride (1:2 by volume) and placed in a 2 L three-neck flask along with the powdered potassium carbonate. This mixture was stirred with an overhead mechanical stirrer to form a slurry. Fumaryl chloride dissolved methylene chloride (1:1 volume ratio) was added dropwise to the slurry. The reaction mixture was maintained at 50° C. (by altering the rate of the fumaryl chloride addition) under a nitrogen blanket. Additional fumaryl chloride was added as needed to facilitate stirring. Upon completion of the fumaryl chloride addition, the mixture was transferred to centrifuge tubes and spun down for 15 minutes at 4000 rpm until the potassium carbonate was completely removed. The supernatant was then added dropwise to petroleum ether to force the polymer out of solution, and the precipitate was rotary-evaporated to yield an amber-colored viscous liquid. Table 1 shows the formulations for polymerizing PEGF.

TABLE 1

| | Fumaryl chloride | PEG diol | $K_2CO_3$ | Methylene chloride for PCL | Methylene chloride for fumaryl chloride |
|---|---|---|---|---|---|
| PEGF 1K | | | | | |
| $M_w$ (g/mol) | 153 | 1111 | 138 | | |
| Mole | 0.09 | 0.09 | 0.135 | | |
| Weight (g) | 13.77 | 100 | 18.63 | | |
| Volume (mL) | 9.73 | ~91.5 | | ~183 | 9.73 |
| PEGF 3.4K | | | | | |
| $M_w$ (g/mol) | 153 | 3350 | 138 | | |
| Mole | 0.0323 | 0.0323 | 0.0484 | | |
| Weight (g) | 4.94 | 108.2 | 6.69 | | |
| Volume (mL) | 3.50 | ~100 | | ~200 | 3.50 |
| PEGF 10K | | | | | |
| $M_w$ (g/mol) | 153 | 8799 | 138 | | |
| Mole | 0.0227 | 0.0227 | 0.0341 | | |
| Weight (g) | 3.48 | 200 | 4.71 | | |
| Volume (mL) | 2.46 | ~183 | | ~366 | 2.46 |

B. Synthesis of Poly(ethylene glycol fumarate)-co-Poly(caprolactone fumarate)

PEG3.4K and PCL1250 with an equal weight of 50 grams were dried together by an azeotropic distillation in toluene and then evacuated under reduced pressure to remove residual traces of water. Fumaryl chloride, the total amount of hydroxyl functional group in the mixture of PEG and PCL, and $K_2CO_3$ were measured out in a 1:1:1.5 molar ratio. The mixture of PCL diols and PEG formed earlier was dissolved in methylene chloride (1:2 by volume) and placed in a 2 L three-neck flask along with the powdered $K_2CO_3$. This mixture was stirred with an overhead mechanical stirrer to form slurry. Fumaryl chloride dissolved in methylene chloride (1:1 volume ratio) was added dropwise to the slurry. The reaction mixture was maintained at 50° C. with nitrogen. Additional fumaryl chloride was added as needed to facilitate stirring.

C. Characterizations

Gel Permeation Chromatography (GPC) was used to determine the molecular weight and polydispersity of the polymers herein. The GPC was carried out with a Waters 717 Plus autosampler GPC system (Waters, Milford, Mass., USA) connected to a Model 515 HPLC pump and Model 2410 refractive index detector. Fourier Transform Infrared Spectroscopy (FTIR) spectra were obtained on a Nicolet 550 spectrometer. All polymers were analyzed using a zinc selenide ATR crystal. The resolution of the instrument was specified as 4 $cm^{-1}$ at a wavenumber of 1000 $cm^{-1}$. Proton and carbon Nuclear Magnetic Resonance (NMR) spectra were acquired on Varian Mercury Plus NMR spectrometer ($^1H$=400.1 MHz, $^{13}C$=100.6 MHz) using $CDCl_3$ solutions containing TMS. Differential Scanning Calorimetry (DSC) was measured on a TA Instruments DSC Q1000 differential scanning calorimeter at a heating rate of 10° C./min in a nitrogen atmosphere. To keep the same thermal history, each sample was preheated from room temperature to 1000° C. and cooled to −90° C. at a cooling rate of 5° C./min. Then the DSC scan was recorded via heating from −90° C. to 100° C. Thermogravimetric Analysis (TGA) was done using a TA model Q500 thermal analyst. The TGA data were obtained in flowing nitrogen at a heating rate of 20° C./min. The molecular characteristics and physical properties of the polymers are shown in Table 2.

D. Crosslinking Process and Scaffold Fabrication

1. Thermal-Crosslinking Process

Benzoyl peroxide (BPO) and N-dimethyl toluidine (DMT) were used as the free radical initiator and accelerator, respectively. A typical procedure for fabrication of scaffolds was as follows. One hundred microliters of initiator solution (50 mg of BPO in 250 microliters of NVP) and 40 microliters of accelerator solution (20 microliters of DMT in 980 microliters of methylene chloride) were added in 1.5 grams PEGF-co-PCLF (or PEGF/PCLF, PEGF/PPF blends) solution in 500 microliters of methylene chloride and mixed thoroughly. The polymerizing scaffold was transferred into various Teflon molds, such as multi-channel tube mode. The mold was placed in a convection oven for overnight to facilitate crosslinking. After crosslinking, cylinders or tubes were removed from the mold before the mold was cooled to ambient temperature.

2. Photocrosslinking Process

Photocrosslinking were initiated with ultraviolet (UV) (λ=380-315 nm) using a photoinitiator bisacylphosphinoxide (BAPO, Ciba Geigy). About 75 μL of BAPO solution in methylene chloride (300 mg BAPO in 1.5 mL methylene chloride) was added into 1.5 g PEGF-co-PCLF (or PEGF/PCLF, PEGF/PPF blends) solution in 500 microliters of methylene chloride and mixed thoroughly. The mixture was poured in a mold formed by two glass plates and a Teflon spacer of 1 mm thickness and the mold was placed directly

TABLE 2

| Polymer | $M_w$ (g mol$^{-1}$) | $M_n$ (g mol$^{-1}$) | DPI | %$_{PCL/PEG}$ (wt. %) Feed Ratio | %$_{PCL/PEG}$ (wt. %) NMR | $[\eta]^a$ (dL · g$^{-1}$) | Tg (° C.) | $T_m$ (° C.) | $\Delta H_m$ (J/g) | $X_c$ (%) | $T_d$ (° C.) |
|---|---|---|---|---|---|---|---|---|---|---|---|
| PCL530 | 1270 | 770 | 1.65 | 100 | 100 | 0.04 | −80.6 | 26.2 | 52.2 | 38.6 | 354 |
| PCL1250 | 3030 | 1710 | 1.77 | 100 | 100 | 0.07 | −73.5 | 43.4 | 61.1 | 45.3 | 386 |
| PCLF530 | 6050 | 3520 | 1.72 | 91.4 | 89.5 | — | −59.1 | 29.2 | 46.2 | 37.4 | 387 |
| PCLF1250 | 15800 | 9000 | 1.76 | 95.7 | 94.3 | 0.19 | −62.7 | 43.9 | 61.0 | 47.2 | 399 |
| Crosslinked PCLF530 | — | — | — | 91.0 | — | — | −54.5 | 27.5 | 1.27 | 0.01 | — |
| Crosslinked PCLF1250 | — | — | — | 95.7 | — | — | −58.5 | 35.7 | 26.8 | 20.7 | — |
| PEG1K | 1250 | 1110 | 1.12 | 100 | 100 | 0.04 | — | 37.7 | 117.7 | 61.3 | 369 |
| PEG3.4K | 4280 | 3880 | 1.10 | 100 | 100 | 0.11 | — | 58.7 | 179.5 | 89.3 | 390 |
| PEG10K | 10900 | 8800 | 1.24 | 100 | 100 | 0.20 | — | 66.3 | 165.9 | 81.3 | 405 |
| PEGF1K | 6870 | 3590 | 1.91 | 93.3 | 92.9 | 0.11 | — | 36.9 | 103.1 | 50.1 | 395 |
| PEGF3.4K | 23300 | 12800 | 1.81 | 97.7 | 95.7 | 0.50 | — | 52.6 | 86.5 | 42.0 | 405 |
| PEGF10K | 19700 | 10900 | 1.81 | 99.1 | 97.9 | 0.35 | — | 58.1 | 148.8 | 72.3 | 404 |
| PCLF-co-PEGF | 12300 | 7230 | 1.70 | 96.7[b] | 95.8 | 0.19 | −59.7 | 50.0 | 85.9 | 52.1[d] | 402 |
| Crosslinked PEGF1K | — | — | — | 93.3 | — | — | — | 32.5 | 52.7 | 27.4 | — |
| Crosslinked PEGF3.4K | — | — | — | 97.7 | — | — | — | 48.6 | 68.6 | 34.1 | — |
| Crosslinked PEGF10K | — | — | — | 99.1 | — | — | — | 56.1 | 102.8 | 50.4 | — |
| Crosslinked PCLF-co-PEGF | — | — | — | 96.7[b] | — | — | −58.6 | 51.8[c] 43.7[c] | 40.3 | 24.5[d] | — |

[a]Intrinsic viscosity was measured in toluene at 30.0 ± 0.05° C.
[b]The total weight ratio of PCL and PEG.
[c]The exothermic peak at 51.8° C. is rather weak compared to the strongest peak at 43.7° C.
[d]Calculated using the average $\Delta H_m^c$ of those of PCL and PEG, 170.4 J/g.

under UV light for 30 minutes to facilitate crosslinking. Therefore, such self- and photo-crosslinkable copolymers are useful to construct tissue-engineering scaffolds using a variety of fabrication methods such as stereolithography.

3. Scaffold Fabrication

Similar crosslinking process can be done to the mixture of PEGF-co-PCLF (or PEGF/PCLF, PEGF/PPF blends) and porogen (salt with various size distributions) to make scaffolds with different porosity, which can be controlled by the content of porogen. After crosslinking, salt was leached out by place the scaffolds in distilled water for 3 days, during which time water changes frequently. The scaffolds were dried in vacuum for at least 12 hours. Solid-form fabrication method and lithostereography can be also used to make PEGF-co-PCLF (or PEGF/PCLF, PEGF/PPF) scaffolds.

E. Swelling Test

The crosslinked PEGF-co-PCLF (or PEGF/PCLF, PEGF/PPF blends) films were made by the above chemical crosslinking process in a mold formed by two glass plates and a Teflon spacer of 1 mm. thickness. The films were cut into some small rectangular cubes (10 mm×5 mm). Two cubes were immersed in excess methylene chloride and water, respectively. After one week, the cubes were taken out of the solvents and their surfaces were dried by blotting before the weight measurement. After that, the solvents in the cubes were evacuated in a vacuum oven for 2 hours and the dry cubes were weighed. The swelling ratios can be determined by the following equation:

$$\text{Swelling ratio} = \frac{W_s - W_d}{W_d} \times 100\%$$

where $W_d$ and $W_s$ are weights of the dry and swollen cubes, respectively.

Figure 8A:
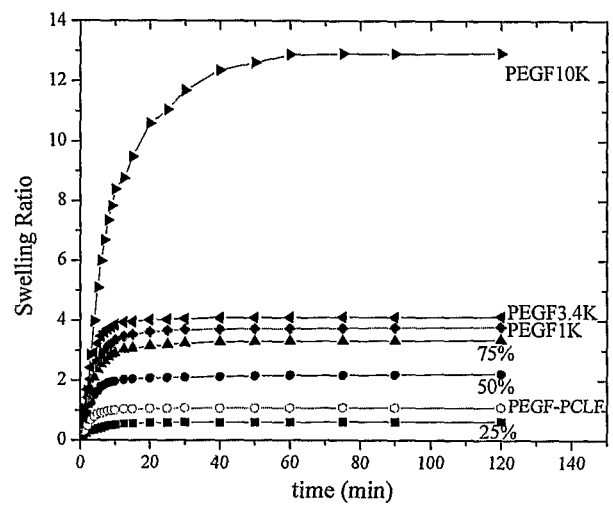
FIG. 8*a* shows swelling ratios of various polymer networks in water as a function of time (25%, 50%, and 75% stand for the PEGF3.4K compositions in the hybrid network).
Figure 8B:
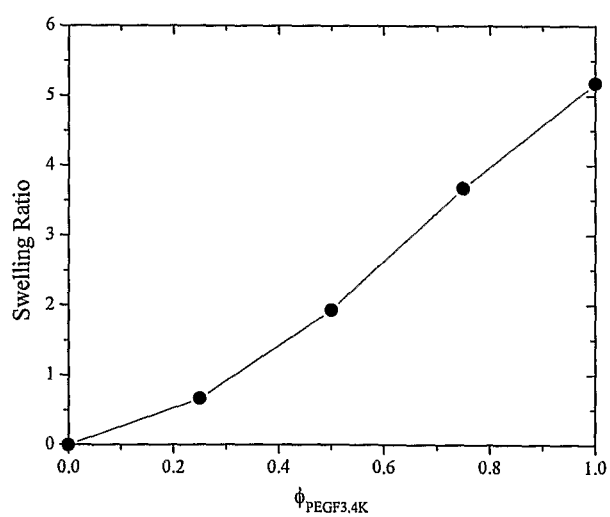
FIG. 8*b* shows swelling ratios of hybrid network formed by the blends of PEGF3.4K and PCLF530 with various PEGF3.4K compositions.

The crosslinked PEGF have been investigated to show the swelling properties in aqueous environment. The swelling ratio increases with the length of PEG used for making PEGF, as shown in FIG. 8a. Since PCLF is hydrophobic, it cannot adsorb water; however, it swells significantly in organic solvents such as methylene chloride and tetrahydrofuran. The amphiphilicity of PEGF-co-PCLF can be confirmed by the average swelling ratios of 106% (FIG. 8a) and 508% in water and methylene chloride, respectively. It also offers one approach to control the swelling ratio of hydrogels by modulating the compositions and block lengths of both hydrophilic and hydrophilic components. The hybrid polymer network formed by the blends of PEGF3.4K and PCLF530 with various PEGF3.4K compositions in FIG. 8b showed controllability of swelling ratios, ranging from 0 for PCLF530 network to 4.5 for PEGF3.4K network. All those copolymers are suitable to copolymerize (or co-crosslink) with other unsaturated monomers, macromers, and polymers for preparation of a variety of materials with different physical properties.

Thus, improved methods for preparing poly(ethylene glycol fumarate) and methods for chemically crosslinking or photocrosslinking poly(ethylene glycol fumarate) with hydrophobic polymers such as poly(propylene fumarate) and poly(caprolactone fumarate) to form various hydrogels with controllable hydrophilicity are provided. The hydrogels are useful as a biocompatible, bioresorbable, injectable, and in-situ hardening scaffold for tissue engineering applications and controlled drug release applications.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A crosslinkable, biodegradable material comprising:
a copolymer comprising:
poly(ethylene glycol fumarate) and
poly(caprolactone fumarate), wherein at least one of the poly(ethylene glycol fumarate) or the copolymer is prepared in the presence of potassium carbonate; and
a free radical initiator or photoinitiator;
wherein the swelling ratio of the material in water or organic solvents is controllable, and the swelling ratio of the material in water is at least about 100% after about 10 minutes of immersion in water.

2. The material of claim 1 wherein:
the material is self-crosslinkable.

3. The material of claim 1 wherein:
wherein the material is an injectable bone substitute.

4. The material of claim 1 further comprising:
a porogen.

5. The material of claim 1 further comprising:
an accelerator.

6. The material of claim 1 wherein:
the material does not include a crosslinking agent.

7. The material of claim 1 further comprising:
particulate or fiber reinforcement materials.

8. The material of claim 1 further comprising:
a bioactive agent.

* * * * *

UNITED STATES PATENT AND TRADEMARK OFFICE
CERTIFICATE OF CORRECTION

PATENT NO.         : 8,912,247 B2
APPLICATION NO.    : 11/912188
DATED              : December 16, 2014
INVENTOR(S)        : Shanfeng Wang, Lichun Lu and Michael J. Yaszemski It is certified that error appears in the above-identified patent and that said Letters Patent is hereby corrected as shown below:

Title Page, Column 2, line 5 item (56) (Other Publications), please delete "injectalbe," and insert -- injectable, --, therefor;

Page 2, Column 1, line 8 item (56) (Other Publications), please delete "repalr,"" and insert -- repair," --, therefor;

Page 2, Column 1, line 13 item (56) (Other Publications), please delete "repalr:" and insert -- repair: --, therefor;

Page 2, Column 2, line 50 item (56) (Other Publications), please delete ""Sythesis" and insert -- "Synthesis --, therefor;

Page 3, Column 1, line 2 item (56) (Other Publications), please delete "repalr,"" and insert -- repair," --, therefor;

Page 3, Column 2, line 19 item (56) (Other Publications), please delete "repalr,"" and insert -- repair," --, therefor.

Signed and Sealed this
Twelfth Day of January, 2016

Michelle K. Lee
*Director of the United States Patent and Trademark Office*